United States Patent
Koshimura

(10) Patent No.: US 9,863,964 B2
(45) Date of Patent: Jan. 9, 2018

(54) SAMPLE ANALYZER, SAMPLE ANALYZING METHOD, AND PROGRAM DETERMINING DATA END POINTS USED TO CALCULATE TARGET MATERIAL CONCENTRATION

(71) Applicant: Sysmex Corporation, Kobe-shi, Hyogo (JP)

(72) Inventor: Naoto Koshimura, Kobe (JP)

(73) Assignee: SYSMEX CORPORATION, Kobe (JP)

(*) Notice: Subject to any disclaimer, the term of this patent is extended or adjusted under 35 U.S.C. 154(b) by 0 days.

(21) Appl. No.: 15/142,905

(22) Filed: Apr. 29, 2016

(65) Prior Publication Data

US 2016/0327582 A1    Nov. 10, 2016

(30) Foreign Application Priority Data

May 8, 2015  (JP) ................. 2015-096043

(51) Int. Cl.
| | |
|---|---|
| *G01N 33/86* | (2006.01) |
| *G01N 21/82* | (2006.01) |
| *G01N 35/00* | (2006.01) |
| *G01N 21/27* | (2006.01) |
| *G01N 21/77* | (2006.01) |

(52) U.S. Cl.
CPC ........... *G01N 33/86* (2013.01); *G01N 21/272* (2013.01); *G01N 21/82* (2013.01); *G01N 35/00693* (2013.01); *G01N 2021/7783* (2013.01); *G01N 2021/7786* (2013.01); *G01N 2021/825* (2013.01); *G01N 2035/0097* (2013.01); *G01N 2035/00702* (2013.01)

(58) Field of Classification Search
CPC ........ G01N 33/86; G01N 21/82; G01N 35/00; G01N 21/27
USPC ................. 422/67, 72; 436/69, 164
See application file for complete search history.

(56) References Cited

U.S. PATENT DOCUMENTS

| | | | | |
|---|---|---|---|---|
| 4,118,192 A * | 10/1978 | Sawai | ..... | G01N 21/75 356/246 |
| 4,217,107 A * | 8/1980 | Saito | ..... | G01N 33/4905 356/39 |
| 4,252,536 A * | 2/1981 | Kishimoto | ..... | G01N 21/272 356/36 |
| 4,720,787 A * | 1/1988 | Lipscomb | ..... | G01N 21/82 422/73 |
| 6,432,657 B1 * | 8/2002 | Kikuchi | ..... | G01N 33/86 435/13 |
| 6,524,861 B1 * | 2/2003 | Anderson | ..... | G01N 33/86 422/63 |
| 7,010,432 B2 * | 3/2006 | Kermani | ..... | G01N 33/86 435/13 |

(Continued)

OTHER PUBLICATIONS

Sebaugh, J.L. et al., "Defining the Linear Portion of a Sigmoid-Shaped Curve: Bend Points", *Pharmaceutical Statistics*, vol. 2, 2003, 9 pages.

*Primary Examiner* — Arlen Soderquist
(74) *Attorney, Agent, or Firm* — Brinks Gilson & Lione

(57) ABSTRACT

Disclosed is a sample analyzer configured to analyze a concentration of a target material contained in a sample based on a value representing a slope of a regression line which is based on data values included in an interval from a start point to an endpoint. The start point is detected by a predetermined method and the endpoint is detected by a predetermined method.

20 Claims, 13 Drawing Sheets

(56) References Cited

U.S. PATENT DOCUMENTS

| | | | | |
|---|---|---|---|---|
| 7,126,676 | B2* | 10/2006 | Greco | G01N 33/4905 |
| | | | | 356/39 |
| 7,226,777 | B2* | 6/2007 | Kawamura | G01N 33/557 |
| | | | | 356/300 |
| 7,276,376 | B2* | 10/2007 | Katayama | G01N 33/4905 |
| | | | | 435/13 |
| 7,276,377 | B2* | 10/2007 | Carroll | G01N 21/82 |
| | | | | 422/73 |
| 7,355,194 | B2* | 4/2008 | Tobimatsu | G01N 21/51 |
| | | | | 250/573 |
| 7,962,292 | B2* | 6/2011 | Matsuo | G01N 15/12 |
| | | | | 356/39 |
| 2003/0138962 | A1* | 7/2003 | Katayama | G01N 33/4905 |
| | | | | 436/69 |
| 2006/0121617 | A1 | 6/2006 | Henckel et al. | |
| 2006/0204997 | A1 | 9/2006 | Macioszek et al. | |
| 2008/0261254 | A1* | 10/2008 | Weyl | C12Q 1/56 |
| | | | | 435/13 |
| 2010/0235103 | A1 | 9/2010 | Carroll et al. | |
| 2010/0248292 | A1* | 9/2010 | Kuwano | G01N 35/02 |
| | | | | 435/29 |
| 2012/0003745 | A1 | 1/2012 | Yabusaki et al. | |
| 2012/0238026 | A1* | 9/2012 | Hayashi | G01N 33/86 |
| | | | | 436/69 |
| 2014/0255254 | A1 | 9/2014 | Yamaguchi et al. | |
| 2016/0274133 | A1* | 9/2016 | Yabutani | G01N 35/1065 |
| 2016/0291040 | A1* | 10/2016 | Koshimura | G01N 33/86 |
| 2016/0291046 | A1* | 10/2016 | Yabutani | G01N 33/86 |

\* cited by examiner

SAMPLE ANALYZER, SAMPLE ANALYZING METHOD, AND PROGRAM DETERMINING DATA END POINTS USED TO CALCULATE TARGET MATERIAL CONCENTRATION

CROSS REFERENCE TO RELATED APPLICATIONS

This application claims priority from prior Japanese Patent Application No. 2015-096043, filed on May 8, 2015, entitled "SAMPLE ANALYZER, BLOOD COAGULATION ANALYZER, SAMPLE ANALYZING METHOD, AND COMPUTER PROGRAM", the entire contents of which are incorporated herein by reference.

FIELD OF THE INVENTION

The invention relates to a sample analyzer, blood coagulation analyzer, sample analyzing method, and computer. Program.

BACKGROUND

United States Patent Application Publication No. 2014/255254 discloses a blood coagulation analyzer which examines blood coagulation by analyzing time series data optically obtained from a measurement sample prepared by mixing reagent and a sample.

The blood coagulation analyzer disclosed in United States Patent Application Publication No. 2014/255254 performs analysis of the coagulation reaction condition based on time series data. However, the shape of the reaction curve obtained from time series data will differ depending on the sample. In the obtained time series data, the time series data obtained when the reaction has stabilized and is progressing is mixed with time series data which are not obtained during that time. Therefore, it is preferable to extract the time series data obtained when the reaction has stabilized and is progressing from the time series data during measurements prior to performing analysis.

SUMMARY OF THE INVENTION (1) An aspect of a sample analyzer including: a sample preparing part which prepares a measurement sample by mixing a sample and reagent; a measuring part which irradiates light on the measurement sample and obtains time series data representing the change over time of the optical data values; a controller; wherein the controller sets the start point detection interval in part of the acquisition period of the time series data obtained by the measuring part; sets the start point detection interval by detecting a data value within the set start point detection interval as the start point of the interval during which the time series data transition linearly when the data values contained in the set start point detection interval satisfy a first evaluation criteria related to the distribution of the data values, and sequentially shifting one period backward from the set start point detection interval until the start point is detected when the data values contained in the set start point detection interval do not satisfy the first evaluation criteria; detects a data value after the start point which satisfies a second evaluation criteria related to linearity as the end point of the interval; and analyzes the concentration of a target material contained in the sample based on a value representing the slope of a regression line which is based on the data values included in the interval from the start point to the endpoint.

(2) An aspect of a blood coagulation analyzer provides a preparing part which prepares a measurement sample by mixing a blood sample and reagent, a measuring part which irradiates light on the measurement sample and obtains time series data representing the change over time of the data related to light absorbance, and a controller. The controller sets the start point detection interval in part of the acquisition period of the time series data obtained by the measuring part, sets the start point detection interval by detecting a data value within the set start point detection interval as the start point of the interval during which the time series data transition linearly when the data values contained in the set start point detection interval satisfy a first evaluation criteria related to the distribution of the data values, and sequentially shifts one period backward from the set start point detection interval until the start point is detected when the data values contained in the set start point detection interval do not satisfy the first evaluation criteria, detects a data value after the start point which satisfies a second evaluation criteria related to linearity as the end point of the interval, and analyzes the concentration of a target material contained in the sample based on a value representing the slope of a regression line which is based on the data values included in the interval from the start point to the endpoint.

(3) An aspect of a sample analyzing method including: a preparing step of preparing a measurement sample by mixing a sample and reagent; a measuring step of irradiating light on the measurement sample and obtaining time series data representing the change over time of the optical data values; a control step; wherein the control step comprises: setting the start point detection interval in part of the acquisition period of the time series data obtained in the measuring step; setting the start point detection interval by detecting a data value within the set start point detection interval as the start point of the interval during which the time series data transition linearly when the data values contained in the set start point detection interval satisfy a first evaluation criteria related to the distribution of the data values, and sequentially shifting one period backward from the set start point detection interval until the start point is detected when the data values contained in the set start point detection interval do not satisfy the first evaluation criteria; detecting a data value after the start point which satisfies a second evaluation criteria related to linearity as the end point of the interval; and analyzing the concentration of a target material contained in the sample based on a value representing the slope of a regression line which is based on the data values included in the interval from the start point to the endpoint.

(4) An aspect of a non-transitory computer readable storage storing a computer program capable of being executed by a central processing unit in a sample analyzer, irradiates light on a measurement sample prepared by mixing a sample and reagent, and obtains time series data representing the change over time of optical data values measured by a measuring part, the computer program enabling the central processing unit of the sample analyzer to perform functions including: setting the start point detection interval in part of the acquisition period of the time series data obtained by the measuring part; setting the start point detection interval by detecting a data value within the set start point detection interval as the start point of the interval during which the time series data transition linearly when the data values contained in the set start point detection interval satisfy a first evaluation criteria related to the distribution of the data values, and sequentially shifting one period backward from the set start point detection interval until the start point is detected when the data values contained in the set start point detection interval do not satisfy the first evaluation criteria; detecting a data value after the start point which satisfies a second evaluation criteria related to linearity as the end point of the interval; and analyzing the concentration of a target material contained in the sample based on a value representing the slope of a regression line which is based on the data values included in the interval from the start point to the endpoint.

According to the invention, a linear interval of time series data can be obtained.

DETAILED DESCRIPTION OF THE PREFERRED EMBODIMENTS

First Embodiment

The sample analyzer of the first embodiment is a blood coagulation analyzer. The blood coagulation analyzer performs analyses related to the coagulation function of blood by measuring a sample obtained from a subject using a coagulation method, synthetic substrate method, turbidity method, and immunoturbidity method. In the sample analyzer, a blood sample such as blood plasma or the like is used as the sample.

Figure 1:
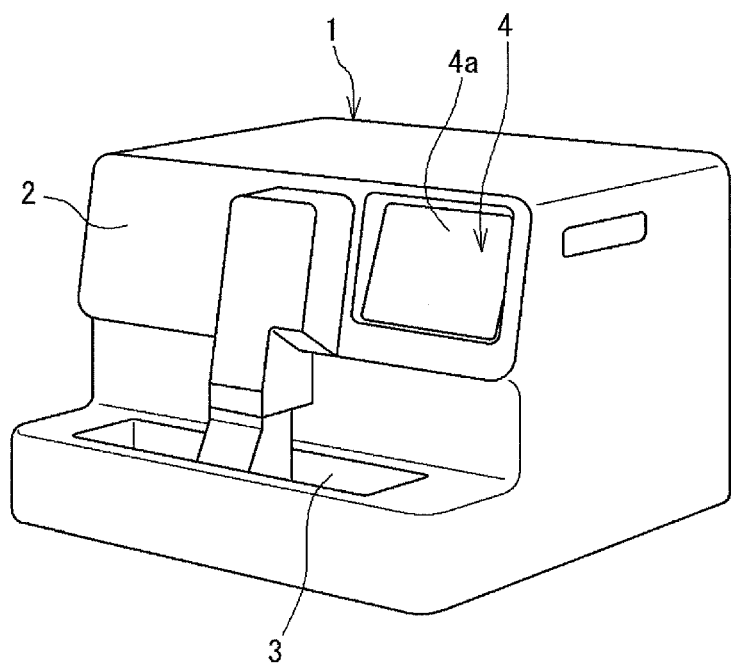
FIG. 1 is a perspective view of the first embodiment of the sample analyzer.

As shown in FIG. 1, the blood coagulation analyzer 1 is provided with a measuring device 2 which optically measures a measurement sample that includes a blood sample such as blood plasma, a sample transporting device 3 which transports a sample container that holds the blood sample and is disposed in front of the measuring device 2, and a control device 4 which issues instructions to the measuring device 2 and analyzes the measurement data obtained by the measuring device 2.

Figure 2:
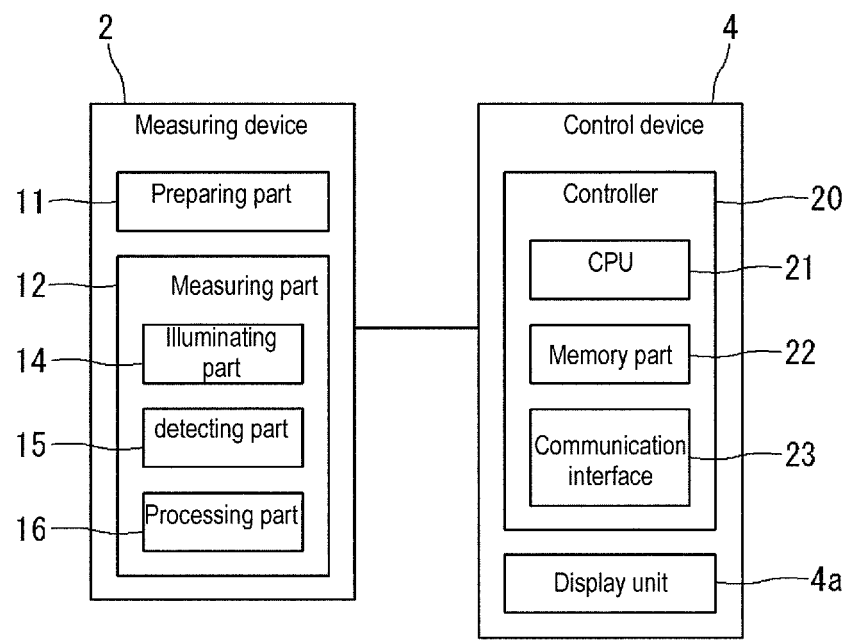
FIG. 2 is a block diagram of the sample analyzer.

As shown in FIG. 2, the measuring device 2 includes a preparing part 11 and a measuring part 12. The preparing part 11 prepares measurement sample by dispensing the reagents held in the reagent containers set in the measuring device 2 and the blood sample held in the sample container that has been transported by the sample transporting device 3 into respective reaction containers, and performing mixing and heating processes. The measurement sample is transported to the measuring part 12, and optical measurements are performed in the measuring part 12. The reagents used in the preparation of the measurement sample differ depending on the measurement sample and the measurement principle, among the coagulation method, synthetic substrate method, turbidity method and immunoturbidity method. When measuring a measurement sample by the immunoturbidity method, a liquid reagent containing particles that carry antibodies which bond to a target substance contained in the sample can be used as the reagent in preparing the measurement sample.

The measuring part 12 is provided with an illuminating part 14 which has a light source such as a halogen lamp, LED or the like, a detecting part 15 which has a light receiving part such as a photodiode or the like, and a processing part 16 which has a CPU, memory and the like. The illuminating part 14 irradiates a predetermined light on the measurement sample. The illuminating part 14 of the first embodiment irradiates the measurement sample with light of wavelengths of a plurality of types according to the measurement item. For example, when performing measurement by the immunoturbidity method, the illuminating part 14 irradiates the measurement sample with light at a wavelength of 800 nm which is spectrally separated by a filter. The illuminating part 14 also irradiates light on the measurement sample for a predetermined time. For example, the illuminating part 14 irradiates the measurement sample with light every 0.1 seconds.

The detecting part 15 receives the light given off by the measurement sample, and outputs electrical signals corresponding to the amount of received light. In particular, the detecting part 15 receives transmitted light, scattered light, fluorescent light and the like from the measurement sample. In measurements using the immunoturbidity method, for example, the measuring part 12 obtains time series data representing the change over time of the optical data values which reflect the degree of cohesion of the particles and the target substance when a liquid reagent containing particles carrying antibodies that bond to a target substance included in the sample is used as the reagent in preparing the measurement sample. More specifically, in measurements using the immunoturbidity method, the illuminating part 14 irradiates the measurement sample with light having a wavelength of 800 nm, and the detecting part 15 receives the transmitted light from the measurement sample. When the agglutination reaction of the immunocomplex proceeds in the measurement sample, the amount of transmitted light received by the detecting part 15 decreases and the output level of the electrical signals is reduced because the turbidity of the measurement sample increases.

The processing part 16 of the measuring part 12 converts the electrical signals of the transmitted light detected by the detecting part 15 to digital data values. The processing part 16 then sends the time series data, which are a collection of converted data values, to the control device 4.

In the measuring part 12, data are obtained of the amount of transmitted light during the predetermined time of one measurement cycle, that is, while the measurement sample is irradiated by light emitted from the illuminating part 14. For example, the measurement sample is irradiated by light for 180 second of one cycle of measurement. When light irradiates every 0.1 seconds, the data values also are obtained every 0.1 seconds. Accordingly, when irradiation is performed for 180 seconds of one cycle of measurement, time series data including 1800 individual data values are obtained.

The control device 4 is provided with a controller 20 and display unit 4a, as shown in FIG. 2. The controller 20 is configured by a CPU 21, Memory part 22 which includes a ROM, RAM, and hard disk, and a communication interface 23. The controller 20 carries out predetermined functions when the CPU 21 executes a computer program stored in the memory part 22. The communication interface 23 is connected to the measuring part 12. The controller 20 sends and receives instruction signals and data with the measuring part 12 through the communication interface 23. Specifically, the controller 20 inputs timer series data concerning the amount of transmitted light, that is, optical measurement signals, received from the processing part 16 of the measuring part 12, through the communication interface 23. The display unit 4a is configured by a liquid crystal monitor or the like.

Figure 3:
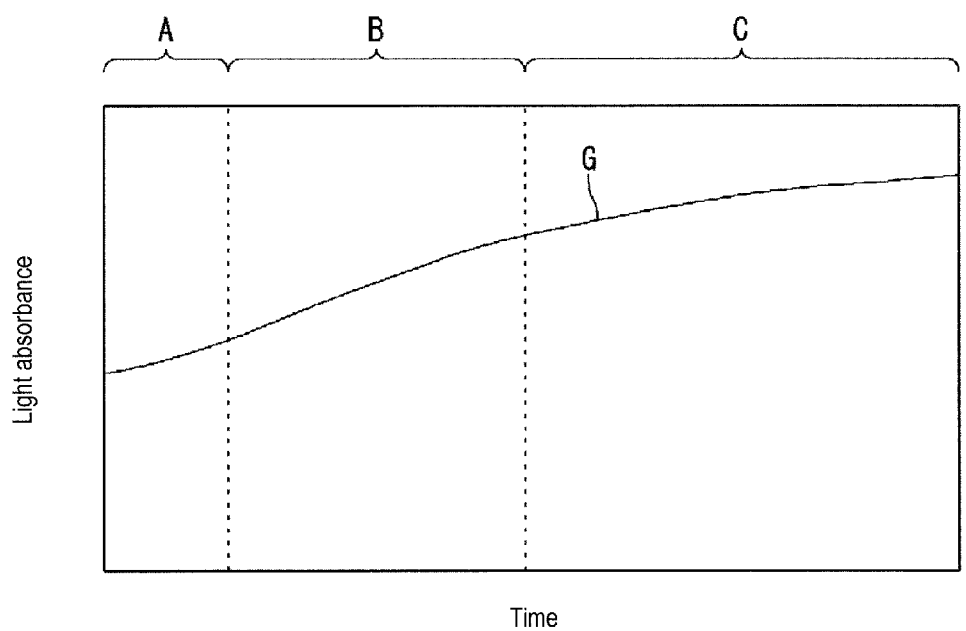
FIG. 3 is a graph showing time series data.

The controller 20 of the control device 4 converts the "transmitted light amount" time series data received from the measuring part 12 to "light absorbance" time series data using a known conversion equation. The controller 20 then smooths the light absorbance time series data via a moving average filter or the like. FIG. 3 shows in graph G the light absorbance time series data converted in the controller 20. The graph of the timer series data obtained from the measurement sample plotted over time, as in graph G, is referred to as a reaction curve. In FIG. 3, the maximum amount of time on the horizontal axis is the measurement time of one cycle, that is, 180 seconds, which is the acquisition period of the time series data.

The light absorbance time series data increases gently in accordance with the passage of time. The absorbance increases gradually during the initial period A of the measurement time in particular, and absorbance increases at a substantially constant rate in the subsequent period B. The degree of increase in absorbance gradually moderates in period C in the latter half of the measurement time. Accordingly, the time series data transition in a substantially S-shaped curve. The rise of light absorbance represents the progress of the reaction in the measurement sample.

The controller 20 of the control device 4 of the embodiment extracts the time series data of the interval during which the reaction progresses stably, and analyzes the time series data of this interval as the target data. In the example shown in FIG. 3, the interval B, in which light absorbance rises linearly at a constant rate, can be regarded as the interval in which the reaction progresses most stably. The control device 4 of the embodiment extracts the "linear interval", that is, the interval in which time series data progress linearly.

The controller 20 of the control device 4 has the function of performing processing to detect the start point of the linear interval, and the function of performing processing to detect the endpoint of the linear interval, in order to extract the linear interval. The controller 20 also performs analyses regarding coagulation function using the extracted linear interval as the target of analysis. The specific processes of the controller 20 of the control device 4 are described below using the diagrams of FIG. 3 through FIG. 7 and the flow charts of FIG. 8 through FIG. 10.

Figure 8:
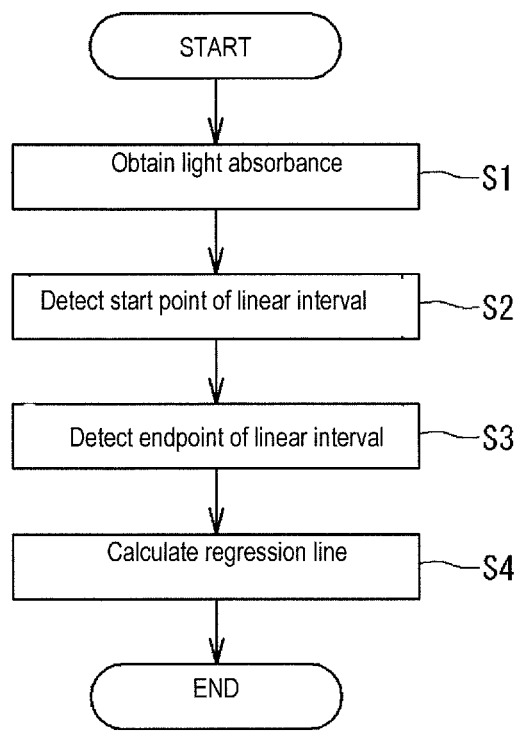
FIG. 8 is a flow chart showing the sequence of processing of a control device.

The controller 20 of the control device 4 converts the "transmitted light" time series data received from the measuring device 2 into "light absorbance" time series data in step S1 of FIG. 8. The controller 20 of the control device 4 also performs processing to detect the start point of the linear interval from the light absorbance time series data in step S2. The sequence of this process is shown in FIG. 9.

Figure 4A:
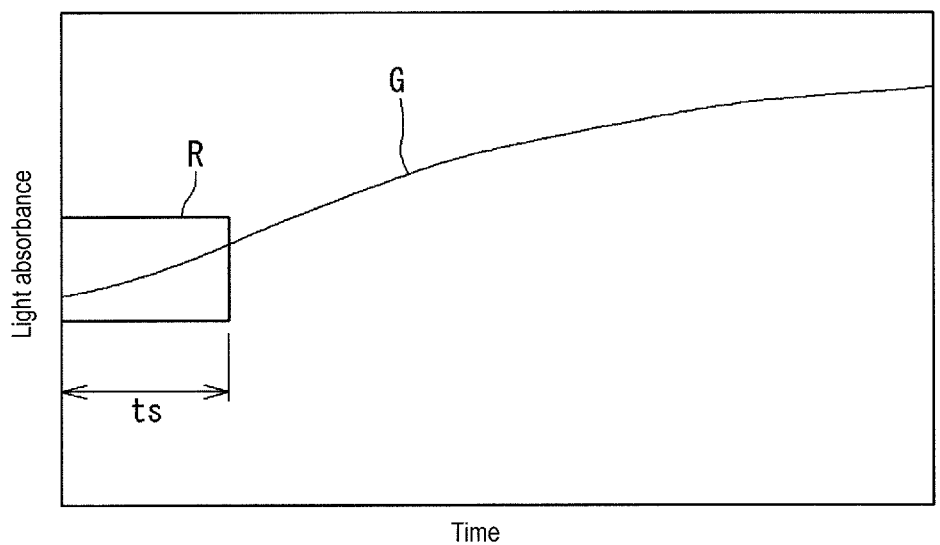
FIG. 4A is a graph showing the start point detection interval, and 4(b) is a graph describing the displacement of the start point detection interval.
Figure 9:
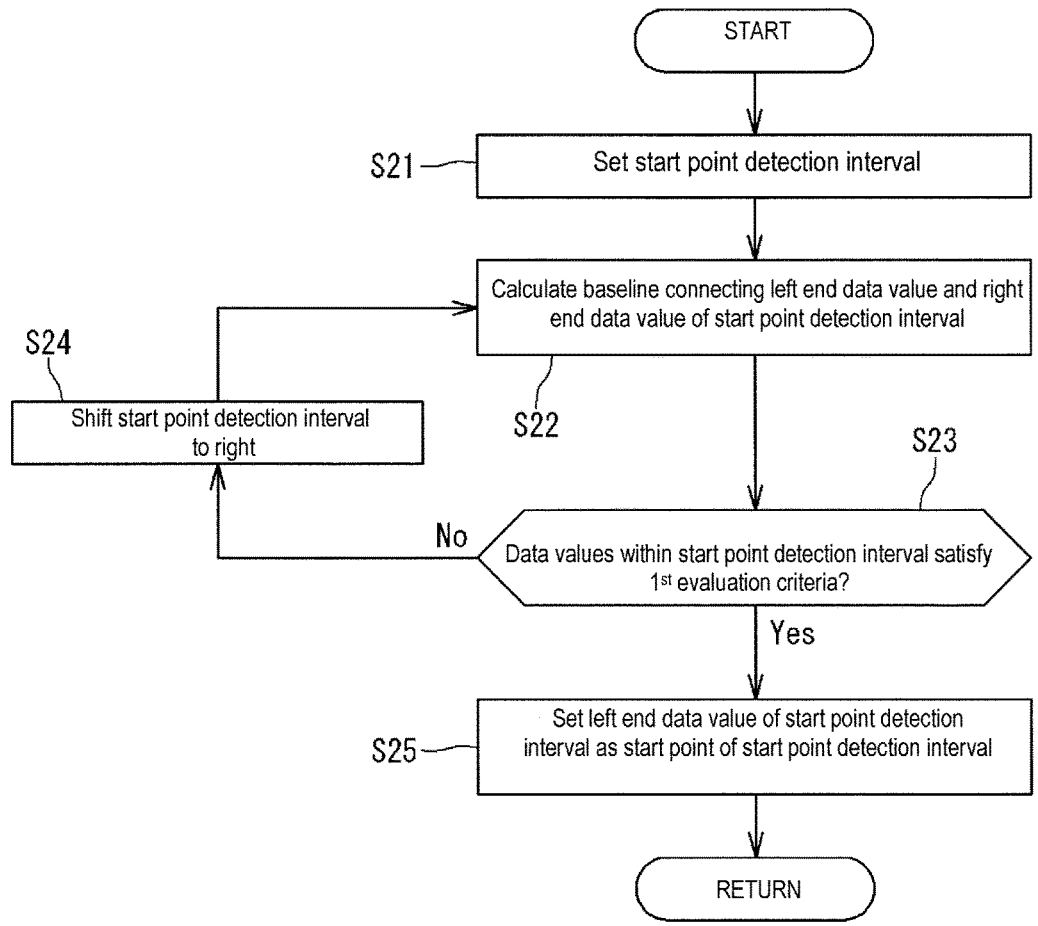
FIG. 9 is a flow chart showing the sequence of the start point detection process of the linear interval.

In step S21 of FIG. 9, the controller 20 sets the start point detection interval in part of the acquisition period of the light absorbance time series data. FIG. 4A shows the start point detection interval R circumscribed by a rectangular frame. The period is of the start point detection interval R is set at, for example, 45 seconds. The controller 20 first sets the start point detection interval R at the beginning of the acquisition period of the time series data.

Figure 5:
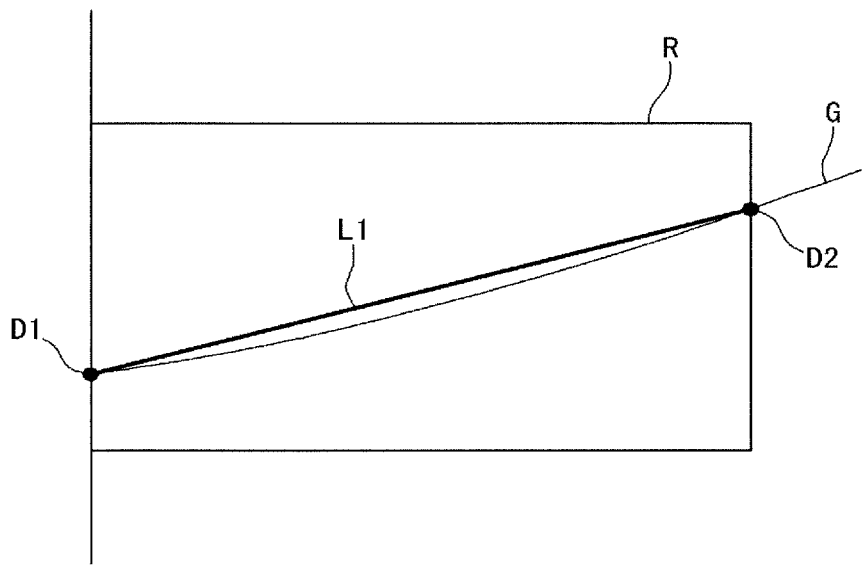
FIG. 5 is a graph showing an enlargement of the start point detection interval.

In step S22 of FIG. 9, the controller 20 sets a straight line L1 connecting the initial data value D1 positioned on the left end of the start point detection interval R, and the final data value D2 positioned at the right end, as shown in FIG. 5. The straight line L1 is referred to as the "baseline".

In step S23 of FIG. 9, the controller 20 determines whether the time series data within the start point detection interval R satisfies a first of the evaluation criteria. Specifically, the controller 20 determines whether the shape of the graph G within the start point detection interval R is convex downward based on the distribution of data values within the start point detection interval R. When the shape of the graph G is convex downward, it is determined that the graph G does not satisfy the first of the evaluation criteria. This is due to at least the first of the data values within the start point detection interval R does not form a linear interval of time series data.

In step S23, the controller 20 compares all data values within the start point detection interval R and the baseline L1, and determines whether each of the data values is a lower value than the baseline L1. Then, when the proportion of data values which are lower values than the baseline L1 is less than a predetermined threshold value among all data values within the start point detection interval R, the graph G is not convex downward and it is determined that the data values within the start point detection interval R satisfy the first evaluation criteria. The predetermined threshold value, for example, may be set at 50%. In this case, it is determined that the graph G is not convex downward if fewer than half the data values which are lower than the baseline L1 are data values within the start point detection interval R.

When the data values within the start point detection interval R have been determined to satisfy the first evaluation criteria in step S23 of FIG. 9, the process advances to step S25, whereas the process advances to step S24 when it is determined that the first of the evaluation criteria is not satisfied. The controller 20 determines the data value at the left end of the start point detection interval R as the start point S1 of the linear interval in step S25.

Figure 4B:
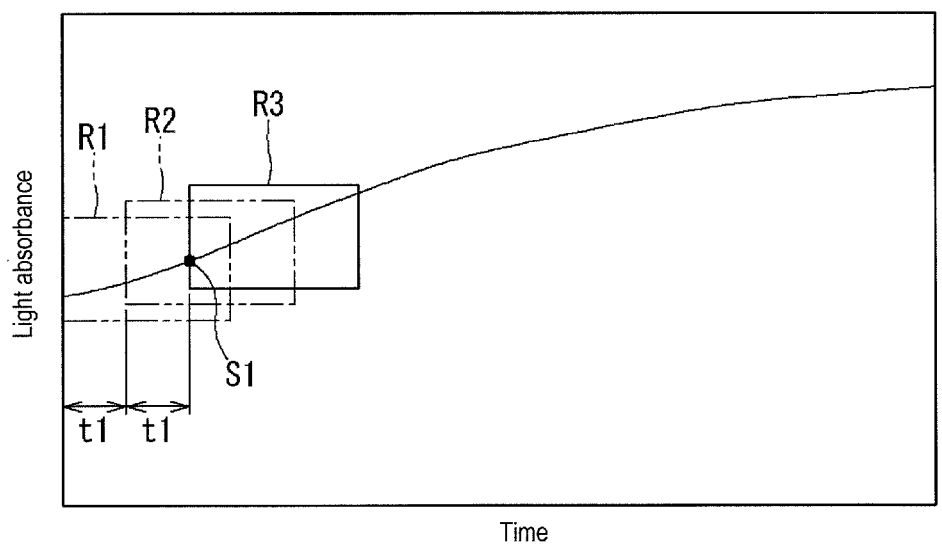

When the data values within the start point detection interval R are found to not satisfy the first of the evaluation criteria, the controller 20 shifts the start point detection interval R to the right side in step S24, and executes the processes of steps S22 and S23 for the newly set start point detection interval R. FIG. 4B shows an example of the process for setting a start point detection interval R3 when the start point S1 cannot be determined in either the newly set start point detection interval R1, or the subsequently set start point detection interval R2.

The start point detection intervals R1 through R3 are set by shifting one by one a predetermined period t1. The period t1, for example, can be set at 1 second. If the data values of the time series data are obtained every 0.1 seconds, the starting point detection intervals R1 through R3 can be set to be shifted after each ten data values. In FIG. 4B, the data value at the left end of the start point detection interval R3 is set as the start point S1 of the linear interval. The period t1 may be suitably set with consideration of the time required for analysis, for example, is of 1/100 or greater but not more than 1/10.

Figure 6:
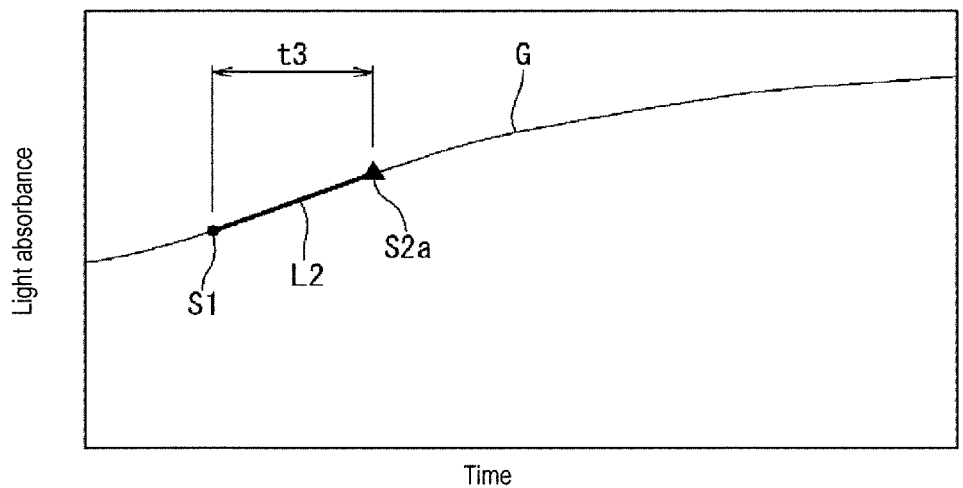
FIG. 6 is a graph describing the endpoint detection process.
Figure 10:
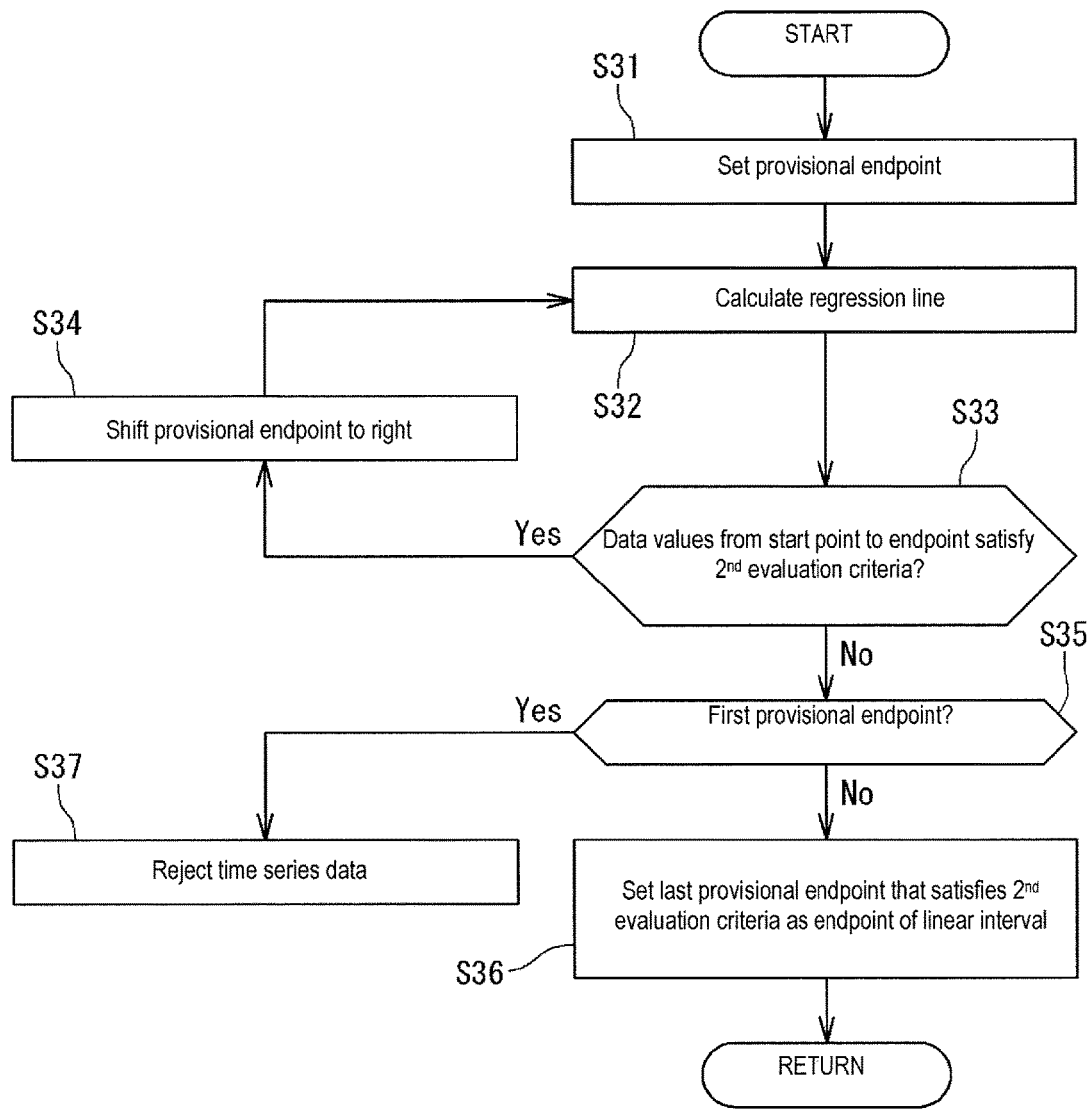
FIG. 10 is a flow chart showing the sequence of the endpoint detection process of the linear interval.
Figure 11:
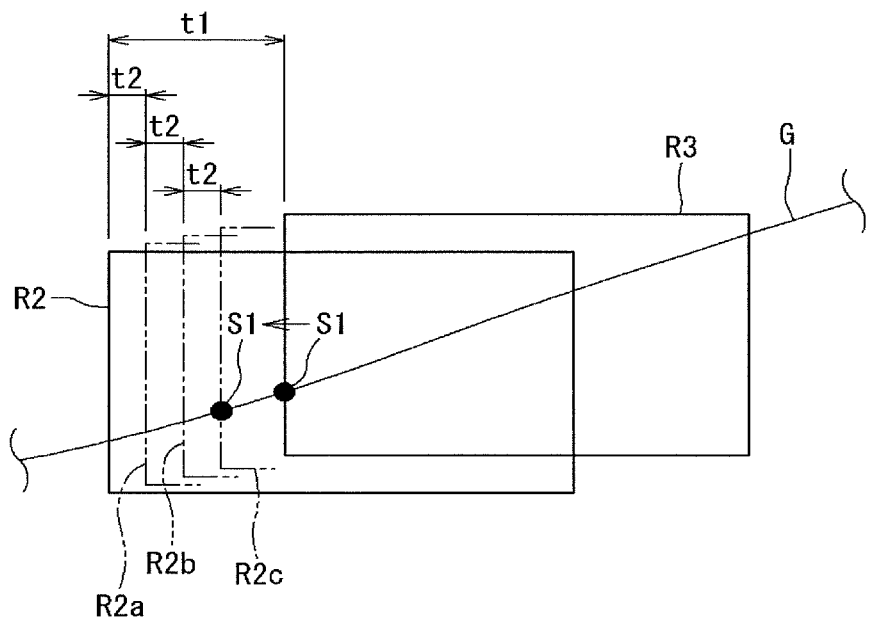
FIG. 11 is a graph describing the start point detection process of a second embodiment.

Returning to FIG. 8, the controller 20 of the control device 4 executes a process to detect the endpoint of the linear interval in step S3. The process is shown in FIG. 10. In step S3 of FIG. 10, the controller 20 sets a provisional endpoint. As shown in FIG. 6, the provisional endpoint S2a is a data value after a predetermined period t3 from the start point S1 set in step S2 of FIG. 8. The predetermined period t3, for example, may be 10 seconds. The period t3 may be suitably set with consideration of the time required for analysis and precision of analysis, for example, is of 1/10 or greater but not more than 1/2.

In step S32 of FIG. 10, the controller 20 calculates a regression line L2 using the data values from the start point S1 to the provisional endpoint S2a, as shown in FIG. 6. The regression line L2 is determined by the least square method or the like, and is a straight line approximating the data values from the start point S1 to the provisional endpoint S2a.

In step S33 of FIG. 10, the controller 20 determines whether the data values from the start point S1 to the provisional endpoint S2a satisfy a second evaluation criteria. Specifically, the deviance between the regression line L2 and the data values from the start point S1 and the provisional endpoint S2a is determined, and the second evaluation criteria is satisfied when the deviance is less than a predetermined threshold value. In the embodiment, the variance value Ve of the residual represented by the following equation is used as an index indicating the deviance. When the variance Ve of the residual is less than a predetermined threshold value, the deviance between the regression line and the data decreases, and the data values progress linearly.

$$Ve = \frac{\sum \{(Reg - OD)^2\}}{n - 2}$$ Equation 1

Note that OD is the data value, Reg is the value on the regression line corresponding to OD, n is the number of data values from the start point S1 to the provisional endpoint S2a.

When the controller 20 determines that the data values from the start point S1 to the provisional endpoint S2a do not satisfy the second evaluation criteria, the process advances to step S35. In step S35, the controller 20 determines whether the provisional endpoint S2a was the initially set provisional endpoint. When the initially set provisional endpoint S2a does not satisfy the second evaluation criteria related to linearity, there is a high probability that reliability is low for use as time series data for analyzing the linear interval because linearity cannot be determined in the extremely short period t3 from the start point S1. Accordingly, the controller 20 rejects the time series data and ends the process in step S37.

When the controller 20 determines that the data values from the start point S1 to the provisional endpoint S2a satisfy the second evaluation criteria in step S33 of FIG. 10, that is, when the controller 20 determines there is a high probability of linearity of the data values from the start point S1 to the provisional endpoint S2a, the process advances to step S34. In step S34, the controller 20 shifts the provisional endpoint back, and thereafter repeats the processes of steps S32 and S33.

Figure 7:
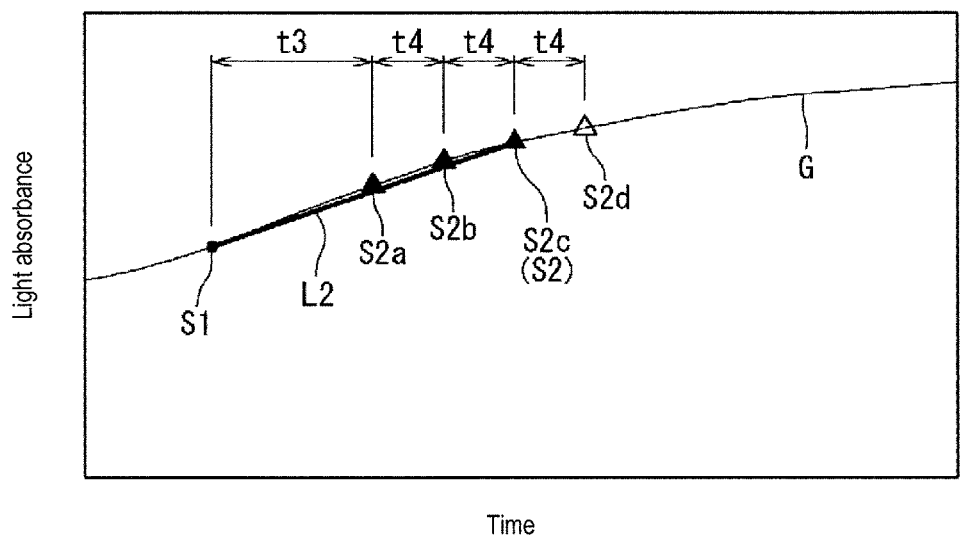
FIG. 7 is a graph describing the endpoint detection process.

Specifically, the controller 20 sets the data value after a predetermined period t4 from the initially set provisional endpoint S2a as the provisional endpoint S2b, as shown in FIG. 7. The period t4 is shorter than the period t3 from the start point S1 to the initial provisional endpoint S2a. Then, a determination is made whether the second evaluation criteria related to linearity is satisfied regarding the provisional endpoint S2b.

When the provisional endpoint S2b satisfies the second evaluation criteria, the controller 20 sets a further provisional endpoint S2c and determines whether the second evaluation criteria is satisfied. This process is repeated, and when the last set provisional endpoint S2d does not satisfy the second evaluation criteria, the controller 20 advances the process to step S36 of FIG. 10. Note that in FIG. 7 the provisional endpoints S2a through S2c which satisfy the second evaluation criteria are represented by black triangles, whereas the provisional endpoint S2d which does not satisfy the second evaluation criteria is represented by a white triangle.

In step S36 of FIG. 10, the controller 20 determines the last provisional endpoint which satisfies the second evaluation criteria will be the endpoint S2 of the linear interval of the time series data, and the process ends. The endpoint S2 positioned a distance from the start point S1 can be set by performing the process described above. Therefore, the liner interval can be set longer, and more accurate analyses can be performed.

Returning to FIG. 8, the controller 20 can analyze the reaction rate by determining the slope of the regression line based on the data values from the set start point S1 to the endpoint S2. The concentration of the target material contained in the sample also can be analyzed based on data of the calibration curve and the slope of the calculated regression line. The data of the calibration curve can be stored in the memory part of the control device 4 to calculate the concentration of the target material in the sample obtained from a subject from the slope of the regression line based on the data values from the start point S1 to the endpoint S2. The calibration curve data are data associated with the slope of a plurality of regression lines obtained by measuring a plurality of standard samples of different known concentrations, and the concentration of the standard samples corresponding to those slopes.

In the above embodiment, when the start point detection interval R is set in part of the acquisition period of the time series data and the data values of the start point detection interval R satisfy the first evaluation criteria related to the distribution of the data values, a data value within the start point detection interval R, and specifically the initial data value, is set as the start point S1 of the linear interval of the time series data. Then a data value which follows the set start point, that is, the most distant data value which satisfies the second evaluation criteria related to linearity, is set as the endpoint S2 of the linear interval. A linear interval during which the reaction proceeds stably can be accurately determined by performing the process described above.

The slope obtained from the linear interval also can be accurately determined with high reproducibility because the slope is extracted from a longer linear interval in the above embodiment. Note that the start point S1 of the linear interval can be any of the data values insofar as the data value is within the start point detection interval R that satisfies the first evaluation criteria. However, a longer linear interval can be extracted by setting the initial data value within the start point detection interval R as the start point S1 of the linear interval.

Figure 13:
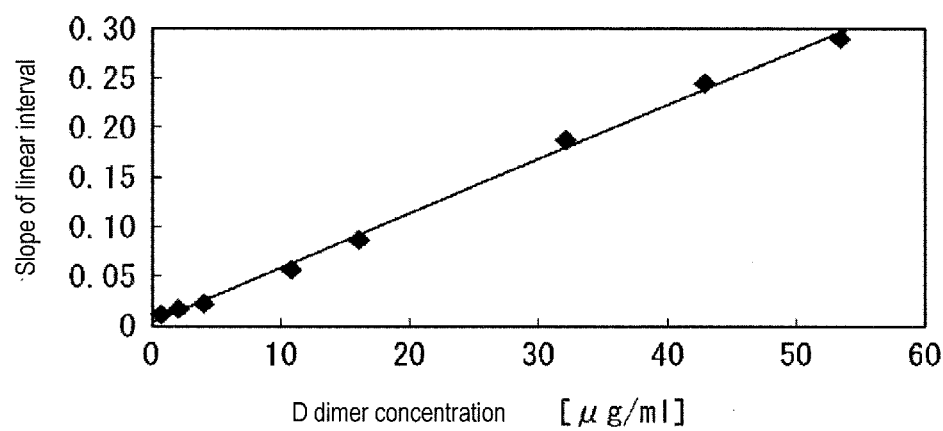
FIG. 13 is a graph evaluating the linear interval obtained by the embodiments.

FIG. 13 shows the slope of a linear interval of time series data obtained by performing a D dimer measurement. In FIG. 13, the D dimer concentration is plotted on the horizontal axis, and the slope of the linear interval of the time series data is plotted on the vertical axis. Each value of the slope was obtained by performing measurement using a measurement sample of known concentration. According to FIG. 13, the slope of the linear interval of the time series data is substantially proportional to the D dimer concentration. Accordingly, it is understood that the D dimer concentration can be suitably analyzed from the slope of the linear interval obtained by the embodiment.

Second Embodiment

In the first embodiment, for example, when the start point detection interval R3 satisfies the first evaluation criteria as shown in FIG. 4B, the initial data value of the start point detection interval R3 is set directly as the start point S1 of the linear interval In the second embodiment, when the start point detection interval R3 satisfies the first evaluation criteria, the start point detection interval R2a is reset at a position shifted back by a period t2 from the immediately previous start point detection interval R2. Then, when this start point detection interval R2a does not satisfy the first evaluation criteria, the start point detection interval R2b is reset at a position shifted back a further period t2, and the same process is repeated until the reset start point interval satisfies the first evaluation criteria up to the start period detection interval R3. When the reset start point detection interval R2c satisfies the first evaluation criteria, the initial data value of the start point detection interval R2c is set as the start point S1 of the linear interval.

The period t2 is set shorter than the period t1. For example, period t2 may be set at 0.1 second relative to period t1 set at 1 second. When the data values used in the time series data are obtained every 0.1 seconds as described above, the start point detection intervals R2 and R3 are set each period t1 of 1 second, and 9 data values exist which are not set as the start point S1 of the linear interval between the start point detection interval R2 and the start point detection interval R3. In the embodiment, the start point detection intervals R2a through R2c are reset using these 9 data values as the lead data value at the point in time it is determined that the starting point detection interval R3 satisfies the first evaluation criteria. By performing this process it is possible to set a previously detected data value as the start point S1 of the linear interval, and a longer linear interval can be extracted.

Note that when none of the reset start point detection intervals R2a through R2c satisfy the first evaluation criteria, the start point detection interval R3 which was determined to satisfy the first evaluation criteria is used as the initial data value of the start point detection interval R3 is used as the start point S1.

Third Embodiment Formal

Figure 12:
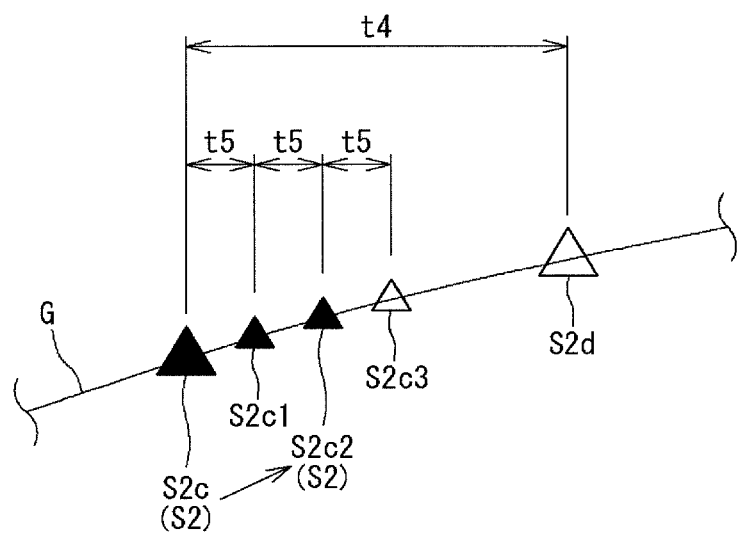
FIG. 12 is a graph describing the endpoint detection process of a third embodiment.

In the previously described first embodiment, for example, the provisional endpoints S2a through S2d are set every period t4, and the provisional endpoint S2c which was the last to satisfy the second evaluation criteria is set as the formal endpoint S2, as shown in FIG. 7. In the third embodiment, when the provisional endpoint S2d which does not satisfy the second evaluation criteria is detected, the provisional endpoints S2ca, S2c2, and S2c3 are reset every period t5 from the immediately previous provisional endpoint S2c, as shown in FIG. 12. Then the provisional endpoint S2c2 which is the very last provisional endpoint to satisfy the second evaluation criteria is reset as the formal endpoint S2 from among the reset provisional endpoints S2c1 through S2c3.

The period t5 is set shorter than the period t4. For example, period t5 may be set at 0.1 second relative to period t4 set at 1 second. When the data values used in the time series data are obtained every 0.1 seconds as described above, the provisional endpoints S2c and S2d are set every each period t4 of 1 second, and 9 data values exist which are not set as the endpoint S2 of the linear interval between the two provisional endpoints S2c and S2d. In the embodiment these 9 data values are sequentially reset from the front as the provisional endpoints S2c1 through S2c3 at the point in time it is determined that the provisional endpoint S2d does not satisfy the second evaluation criteria. By performing this process it is possible to set a data value detected afterward as the endpoint S2 of the linear interval, and a longer linear interval can be extracted.

Note that when none of the reset provisional endpoints S2c1 through S2c3 satisfies the second evaluation criteria, the endpoint S2c which was already determined to satisfy the second evaluation criteria is then set as the formal endpoint S2.

The first through third embodiments in all respects are examples and not to be regarded as limiting in any way. The scope of the invention is defined solely by the appended claims and not affected to any degree by the statements within this summary, and may be variously and appropriately modified insofar as such modification is within the scope of the meaning expressed in the claims.

For example, the invention may be suitably applied to items measured by the immunoturbidity method, for example, measurements of fibrin-fibrinogen degradation products (FDP), D dimer, or von Willebrand factor (vWF). In this case the target materials in the sample to be analyzed for concentration are FDP, D dimer, or vWF, respectively. The invention also may be applied to measurement of other items.

The period ts of the start point detection interval R, which is set to detect the start point of the linear interval of the time series data, is not specifically limited and may be set as is appropriate. When the period ts is too long, however, part of the change in the S-shape mat be included in the start point detection interval R, thereby making accurate evaluation difficult. When the period ts is too short, the process is more susceptible the influence of noise, and accurate evaluation of the data value distribution becomes difficult. From this perspective the period ts of the start point detection interval R must be set shorter than the acquisition period of the time series data, and it is particularly desirable that the period ts is set shorter than 1/3 of the acquisition period. The period ts of the start point detection period R also is preferably longer than 1/30 of the acquisition period of the time series data. The period ts of the start point detection period R, for example, preferably is set longer than the period t1 from the start point S1 to the initial provisional endpoint S2a as shown in FIG. 3.

Although the first through third embodiments are described by way of examples in which the time series data change in an S-shape, the invention may be adapted to, for example, time series data that do not appear convex downward at the beginning of measurement. For example, the invention is applicable to time series data that change linearly with a slight slope from the start of measurement when there is low concentration of target material in the sample, and time series data that change linearly with a steep slope from the start of measurement when there is high concentration of target material in the sample. Therefore, the invention is particularly suitable for measurements in which the shape is unknown such as when the type of shape of the graph obtained from the time series data is unknown, or the shape of a plurality of types including an S-shape and linear shape. For example, the immunoturbidity method can be used for such measurements.

Although time series data of light absorbance is used in the analysis in the above embodiments, time series data of the amount of transmitted light also may be used in analysis. In this case the time series data will have an upward convex shape at the start of measurement due to the low reaction progress. The first evaluation criteria in this case also may be a condition in which the data values that are higher than the baseline L1 are less than a predetermined threshold value, excluding the interval in which the time series data are convex upward.

Although a blood coagulation analyzer is shown as the sample analyzer in the above embodiments, the invention also is applicable to other analyzers.

What is claimed is:

1. A sample analyzer comprising:
   a sample preparing part which prepares a measurement sample by mixing a sample and reagent;
   a measuring part which irradiates light on the measurement sample and obtains time series data representing the change over time of the optical data values;
   a controller;
   wherein the controller is configured to:
   set a first point on the time series data and a second point on the time series data apart from the first point by a predetermined interval;
   calculate a first value related to a distribution of time series data from the first point to the second point based on time series data from the first point to the second point and a base line connecting the first point to the second point;
   shift the first point and the second point backwardly by a second predetermined interval until the calculated first value satisfies a first evaluation criteria;
   set the shifted first point as the start point when the calculated first value satisfies the first evaluation criteria;
   set a provisional end point on the time series data, apart from the start point by the second predetermined interval;
   calculate a second value related to linearity based on the time series data from the start point to a provisional end point and a regression line between the start point and the provisional end point;
   set the provisional end point as an end point when the calculated second value satisfies a second evaluation criteria; and
   analyze the concentration of a target material contained in the sample based on a value representing the slope of a regression line which is based on data values included in an interval from the start point to the endpoint.

2. The sample analyzer of claim 1, wherein the controller detects an initial data value of the start point detection interval as the start point.

3. The sample analyzer of claim 1, wherein the first evaluation criteria uses, as an index, a proportion of the data values which have lower or higher values than the base line connecting an initial data value and a final data value of the start point detection interval among all data values within the start point detection interval;
the controller determines whether the first evaluation criteria is satisfied based on the comparison of the proportion and a first threshold value.

4. The sample analyzer of claim 1, wherein the second evaluation criteria uses, as an index, the deviance between the start point and a later data value, and the regression line set by the start point and a data value after the start point;
the controller determines whether the second evaluation criteria is satisfied based on the comparison of the deviance and a second threshold value.

5. The sample analyzer of claim 1, wherein the controller sets the start point detection interval by sequentially shifting a first period one by one backward from the start of the acquisition period until a start point is detected.

6. The sample analyzer of claim 5, wherein the controller resets the start position detection interval by shifting one by one a second period which is shorter than the first period from the immediately previous start point detection period until a start point is again detected, and determines whether the reset start point detection interval satisfies the first evaluation criteria when a start point is detected in the second and subsequently set start point detection intervals.

7. The sample analyzer of claim 1, wherein the controller sets a data value after a third period has elapsed from the start point as a first provisional endpoint, sets a data value obtained in a fourth period from the first provisional endpoint as a second provisional endpoint when the first provisional endpoint satisfies the first evaluation criteria, and detects either the first provisional endpoint or the second provisional endpoint as the formal endpoint furthest after the second evaluation criteria is satisfied.

8. The sample analyzer of claim 7, wherein the time series data are rejected when the first provisional endpoint does not satisfy the second evaluation criteria.

9. The sample analyzer of claim 7, wherein the controller resets, as the second provisional endpoint, the data value obtained in each fifth period which is shorter than the fourth period from the first provisional endpoint or second provisional endpoint when the second provisional endpoint does not satisfy the second evaluation criteria, and detects the first provisional endpoint or second provisional endpoint furthest after the second evaluation criteria as the formal endpoint.

10. The sample analyzer of claim 7, wherein the period of the start point detection interval is set longer than the third period and shorter than the acquisition period of the time series data.

11. The sample analyzer of claim 10, wherein the period of the start point detection interval is set shorter than ⅓ of the acquisition period of the time series data.

12. The sample analyzer of claim 1, wherein the reagent is a liquid reagent containing particles which carry antibodies that bond with the target material; and the measuring part obtains time series data representing the change over time of the optical data values that reflect the degree of agglutination of the particles and the target material as the time series data.

13. A sample analyzing method comprising:
    a preparing step of preparing a measurement sample by mixing a sample and reagent;
    a measuring step of irradiating light on the measurement sample and obtaining time series data representing the change over time of the optical data values;
    a control step;
    wherein the control step comprises:
    setting a first point on the time series data and a second point on the time series data apart from the first point by a predetermined interval;

calculating a first value related to distribution of the time series data from the first point to the second point based on the time series data from the first point to the second point and a base line connecting the first point to the second point;

shifting the first point and the second point backwardly by a second predetermined interval until the calculated first value satisfies a first evaluation criteria;

setting the shifted first point as the start point when the calculated first value satisfies the first evaluation criteria;

setting a provisional end point on the time series data, apart from the start point by a second predetermined interval;

calculating a second value related to linearity based on the time series data from the start point to a provisional end point and a regression line between the start point and the provisional end point;

setting the provisional end point as an end point when the calculated second value satisfies a second evaluation criteria; and analyzing the concentration of a target material contained in the sample based on a value representing the slope of a regression line which is based on the data values included in an interval from the start point to the endpoint.

14. The sample analyzing method of claim 13, wherein the start point is an initial data value of the start point detection interval.

15. The sample analyzing method of claim 14, wherein the first evaluation criteria uses, as an index, the proportion of the data values which have lower or higher values than the base line connecting an initial data value and a final data value of the start point detection interval among all data values within the start point detection interval, wherein the sample analyzing method further comprises determining whether the first evaluation criteria is satisfied based on the comparison of the proportion and a first threshold value.

16. The sample analyzing method of claim 13, wherein the second evaluation criteria uses, as an index, the deviance between the start point and a later data value, and the regression line set by the start point and a data value after the start point, wherein the sample analyzing method further comprises determining whether the second evaluation criteria is satisfied based on the comparison of the deviance and a second threshold value.

17. The sample analyzing method of claim 13, wherein the start point detection interval is set by sequentially shifting a first period one by one backward from the start of the acquisition period until a start point is detected.

18. The sample analyzing method of claim 17, wherein the start position detection interval is reset by shifting one by one a second period which is shorter than the first period from the immediately previous start point detection period until a start point is again detected, and determines whether the reset start point detection interval satisfies the first evaluation criteria when a start point is detected in the second and subsequently set start point detection intervals.

19. The sample analyzing method of claim 13, wherein the target material is fibrin-fibrinogen degradation products, D dimer, or von Willebrand factor.

20. A non-transitory computer readable storage storing a computer program capable of being executed by a central processing unit in a sample analyzer, irradiates light on a measurement sample prepared by mixing a sample and reagent, and obtains time series data representing the change over time of optical data values measured by a measuring part, the computer program enabling the central processing unit of the sample analyzer to perform functions comprising:

setting a first point on the time series data and a second point on the time series data apart from the first point by a predetermined;

calculating a first value related to distribution of the time series data from the first point to the second point based on the time series data from the first point to the second point and a base line connecting the first point to the second point;

shifting the first point and the second point backwardly by a second predetermined interval until the calculated first value satisfies a first evaluation criteria;

setting the shifted first point as the start point when the calculated first values satisfies a first evaluation criteria;

setting a provisional end point on the time series data, apart from the start point by a second predetermined interval;

calculating a second value related to linearity based on the time series data from the start point to a provisional end point and a regression line between the start point and the provisional end point;

setting the provisional end point as an end point when the calculated second value satisfies a second evaluation criteria; and analyzing the concentration of a target material contained in the sample based on a value representing the slope of a regression line which is based on the data values included in an interval from the start point to the endpoint.

* * * * *